(12) United States Patent
Chan et al.

(10) Patent No.: US 8,709,137 B2
(45) Date of Patent: Apr. 29, 2014

(54) METHOD AND APPARATUS FOR DISINFECTING AND DEODORIZING A TOILET SYSTEM

(75) Inventors: Chi Keung Rudy Chan, Kowloon (HK); Yee Lam Chan, Kowloon (HK); Lam Lung Yeung, Kowloon (HK); Ka Tung Ho, Kowloon (HK)

(73) Assignee: RHI Limited, Fo Tan, N.T, Hong Kong (CN)

( * ) Notice: Subject to any disclaimer, the term of this patent is extended or adjusted under 35 U.S.C. 154(b) by 69 days.

(21) Appl. No.: 13/395,447

(22) PCT Filed: Sep. 11, 2009

(86) PCT No.: PCT/CN2009/073881
§ 371 (c)(1),
(2), (4) Date: Mar. 21, 2012

(87) PCT Pub. No.: WO2011/029236
PCT Pub. Date: Mar. 17, 2011

(65) Prior Publication Data
US 2012/0227586 A1      Sep. 13, 2012

(51) Int. Cl.
*B01D 46/00* (2006.01)

(52) U.S. Cl.
USPC ............. 95/273; 96/223; 55/385.1; 422/4; 4/306; 4/347

(58) Field of Classification Search
USPC .......... 55/385.1, 482; 95/1, 273; 96/222, 397; 261/115; 4/213, 300, 301, 234, 235, 4/367.1, 371, 222, 214–217; 220/200, 220/371, 203.22, 212, 212.5; 422/121–123
See application file for complete search history.

(56) References Cited

U.S. PATENT DOCUMENTS

| | | | |
|---|---|---|---|
| 5,452,481 A * | 9/1995 | Meyer | 4/213 |
| 6,660,060 B2 * | 12/2003 | Chasen | 95/1 |
| 7,485,166 B2 * | 2/2009 | Safuto | 55/385.1 |
| 7,976,600 B1 * | 7/2011 | Safuto | 55/385.1 |
| 8,337,602 B2 * | 12/2012 | Foerster | 96/147 |
| 2009/0169438 A1 * | 7/2009 | Bruggink | 422/121 |

* cited by examiner

*Primary Examiner* — Duane Smith
*Assistant Examiner* — Minh-Chau Pham
(74) *Attorney, Agent, or Firm* — Global IP Services; Tianhua Gu

(57) ABSTRACT

A method and an apparatus are provided for deodorizing and disinfecting air and droplets from urinal, toilet bowl, and other receivers and holders of urine and fecal matter. The apparatus comprises a housing (1) having an air inlet (2) and air outlet (3), wherein the housing (1) encloses a droplet removal chamber (4) for removing droplets from airflow; a deodorization and disinfection chamber (5) for removing air contaminants in the airflow; and an delivery unit (6) for airflow generation. Being actively drawn into the apparatus, air contaminants such as odor, bacteria and virus are removed without discharge of contaminated air and causing secondary pollution. The apparatus and method provide odorless and comfortable environment and avoid disease transmission in both public and domestic toilets.

55 Claims, 4 Drawing Sheets

METHOD AND APPARATUS FOR DISINFECTING AND DEODORIZING A TOILET SYSTEM

FIELD OF THE INVENTION

The present invention relates to a method and an apparatus for deodorizing and disinfecting air from toilets, urinal, toilet bowl, and other receivers and holders of urine and fecal matter. More particularly, it is effective in removing odor, bacteria and virus in toilet without causing secondary pollution.

BACKGROUND OF THE INVENTION

Bad smell in toilet is known to come from urine and fecal matter. Virus such as SARS and bacteria can be transmitted from such excreta to air. When urine is streaming to the wall of urinal, splashing and splitting of urine may be caused, and then small urine droplets and vapor are generated. Some urine droplets will leave the urinal and suspend in air. In addition, such urine and fecal matter cause nuisance odor and pollute toilet environment. Moreover, it is known that droplets and air are always good carriers of odor, bacteria and virus, which can transmit disease. It raises more concern of disease transmission especially in the toilet of infectious disease ward.

Various methods and apparatus have been proposed for deodorization and disinfection of air in toilet but they have their own limitations and disadvantages respectively.

For examples, the inventions disclosed in U.S. Pat. Nos. 6,003,157 and 7,461,410, use a ventilation system to extract contaminated air from toilet bowl and discharge them through air duct to atmosphere. Nevertheless, contaminated air with bacteria or virus is not treated instead of just transferring it to other areas, and eventually, disease will be transmitted.

Other systems use ventilation device to draw contaminated air into an adsorbent filter like activated carbon filter so that air contaminants are adsorbed on the surface of adsorbent materials. However, the adsorption efficiency will be decreased by water droplets and vapor. The adsorbent filter can also serve as a suitable environment for growth and reproduction of bacteria due to high humidity and presence of organic nutrients that leads to secondary pollution.

Most patents, such as U.S. Pat. Nos. 5,991,934 and 7,165,274, focus mainly on gaseous contaminants but is not effective in water droplet extraction, which play even a more important role in this infectious problem.

A toilet seat generating ions to oxidize odor is disclosed by U.S. Pat. No. 6,785,912. However, it is believed that the oxidation rate between ions and odor is low. In addition, the excessive ions may be harmful to human.

Therefore, a heretofore unaddressed need exists in the art to address the aforementioned deficiencies and inadequacies.

SUMMARY OF THE INVENTION

The present invention relates to a method and an air cleaning apparatus for deodorizing and disinfecting air and droplets from toilets, urinals, toilet bowl and other receivers and holders of urine and fecal matter. The present invention can be widely applied in premises such as hospitals, commercial buildings, public toilets, transport interchanges and residential areas.

One aspect of the present invention is to provide an air cleaning apparatus comprising a housing having an air inlet and an air outlet, wherein the housing encloses a droplet removal chamber for removing droplets from airflow, a deodorization and disinfection chamber for removing air contaminants in the airflow and an air delivery unit for airflow generation.

Regarding to the present invention, an air delivery unit having the capacity in generation of airflow to extract droplets and air into the housing through the air inlet is provided, which is located in urinal and toilet bowl. The position, shape and size of air inlet are well designed to achieve sufficient air extraction thus generating negative pressure for trapping contaminated air without spreading. The treated air can either be directly discharged or redirected back to the urinal or toilet blow for re-circulation. An additional blower fan is deployed to form an air curtain on the surface of urinal and toilet bowl for better trapping of contaminated air.

The droplet removal chamber of the present invention, having a water exhaust outlet and enclosing a reactive oxidizing species (ROS) generator and a droplet removal filter, is to remove droplets in airflow. Droplets in the airflow are intercepted by the droplet removal filter, which can be an adsorption and/or a scrubber type. The aggregated droplets are discharged from the deodorization and disinfection chamber through the water exhaust outlet.

The deodorization and disinfection chamber of the present invention, enclosing a reactive oxidizing species generator, a dust filter and an adsorbent filter, is to remove gaseous contaminants. The dust filter can be made of fibrous and cellulose material, which serves to trap dust, airborne bacteria and virus. The adsorbent filter comprises of a porous enclosure and adsorbent materials, which removes gaseous contaminants by confining them into the micro/nanopore of adsorbent materials. The reactive oxidizing species generator releases reactive oxidizing species to eradicate bacteria and virus trapped on the dust filter thereby preventing secondary pollution. In addition, ROS decompose gaseous contaminants into non-harmful products like water molecules and carbon dioxide that results in the rejuvenation of micro/nanopores for further adsorption of air contaminants. In addition, the adsorbent materials are effective in the decomposition of excessive ROS, which are prevented from leakage. An UV light can be installed in the system for further disinfection and production of ROS. The treated air can either be discharged or redirected to urinal or toilet bowl for further air circulation.

Another aspect of the present invention is to provide an air cleaning method for disinfecting and deodorizing a toilet system by employing the air cleaning apparatus according to the present invention, said method comprising the steps:
  a) The air delivering unit is switched on to generate airflow;
  b) Droplets and air from urinal or toilet bowl are extracted into the air cleaning apparatus through the air inlet;
  c) In the droplet removal chamber, droplets from the airflow are removed by the droplet filter;
  d) In the deodorization and disinfection chamber, air contaminants from the airflow are removed;
  e) The treated airflow is either discharged through the air outlet or redirected to urinal or toilet bowl for further circulation.

These and other aspects of the present invention will become apparent from the following description of the preferred embodiment taken in conjunction with the following drawings, although variations and modifications therein may be affected without departing from the spirit and scope of the novel concepts of the invention.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment, and wherein.

DETAILED DESCRIPTION OF THE PREFERRED EMBODIMENT

Figure 1:
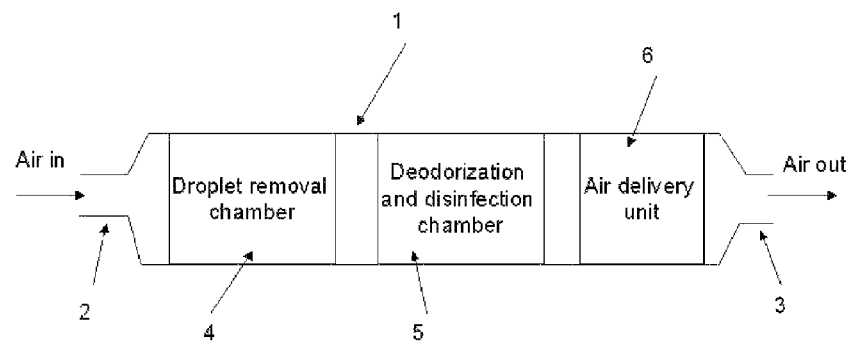
FIG. 1 is a schematic diagram of the air cleaning apparatus according to one embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise.

The description will be made as to the embodiments of the present invention in conjunction with the accompanying drawings in FIGS. 1-7. In accordance with the purposes of this invention, as embodied and broadly described herein, this invention, in one aspect, relates to an air cleaning apparatus.

Referring now to FIG. 1, an air cleaning apparatus according to one embodiment of the present disclosure is shown. The air cleaning apparatus of the present invention comprises of a housing 1 having an air inlet 2 and an air outlet 3. The housing 1 encloses a droplet removal chamber 4, a deodorization and disinfection chamber 5 and an air delivery unit 6. The air delivery unit 6 generates airflow to extract contaminated air and droplets from urinal, toilet bowl and toilet into the air cleaning apparatus. The contaminated air passes through the air inlet 2, the droplet removal chamber 4, and the deodorization and disinfection chamber 5. Eventually, the treated air can either be discharged from the outlet 3 or redirected to urinal for further air circulation.

Figure 2:
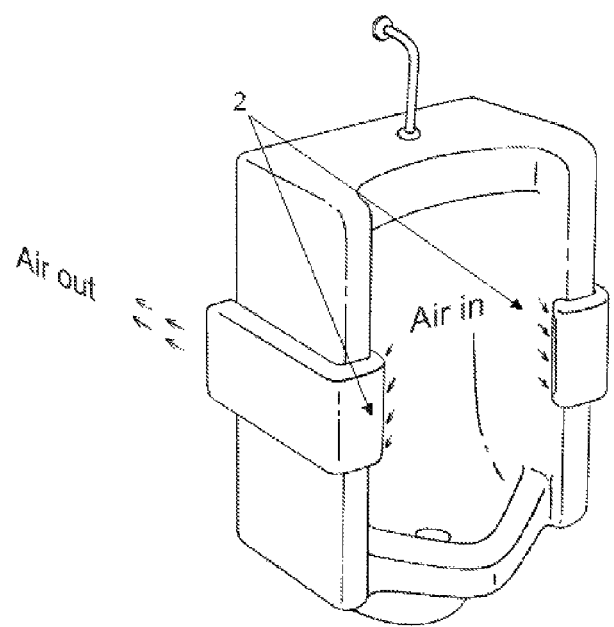
FIG. 2 is a schematic diagram indicating the airflow in the urinal according to one embodiment of the present invention.

FIG. 2 is a schematic diagram indicating the airflow in the urinal according to one embodiment of the present invention. As indicated in FIG. 2, air inlets 2 are located in the lateral sides of urinal. In another embodiment of present invention, the air inlets 2 can be located in the vertical side of the urinal. In a further embodiment of present invention, the air inlets 2 can be located both in the vertical and lateral sides of the urinal. The air inlet discussed here can be one or more, and also can be different size and shape, a variety of which are well-known to those skilled in the art.

When people urinate, the air delivery unit 6 is switched on and the contaminated air is extracted into the air inlets 2. As a negative pressure is developed in urinal by airflow, droplets and contaminated air are confined without spreading. In addition, a blower fan can be installed in the urinal to generate a layer of airflow on the surface of urinal to from an air curtain. It increases the capacity in preventing the leakage of air contaminants from urinal. Extracted into the apparatus by the airflow, droplets and contaminated air enter the droplet removal chamber 4.

Figure 3:
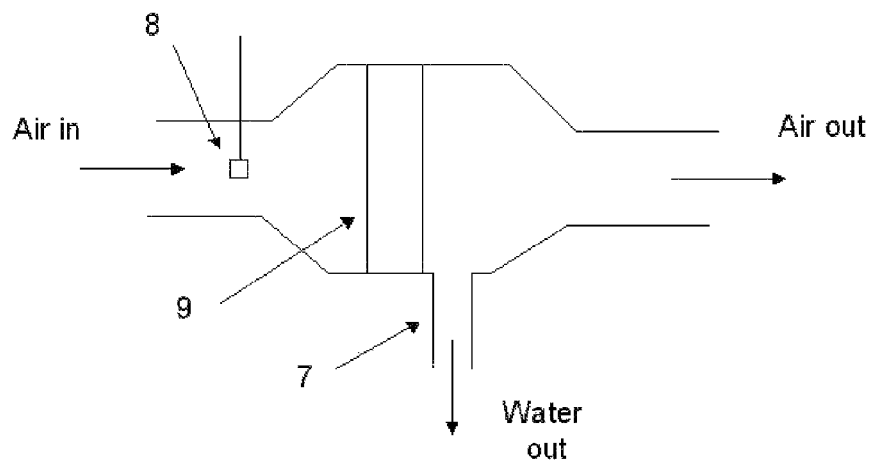
FIG. 3 is a schematic diagram of droplet removal chamber with adsorption droplet filter according to one embodiment of the present invention.

FIG. 3 is a schematic diagram of droplet removal chamber with adsorption droplet filter according to one embodiment of the present invention. As shown in FIG. 3, the droplet removal chamber 4 having a water exhaust outlet 7 encloses a ROS generator 8 and a droplet filter 9. The shape of the droplet removal chamber 4 can be rectangular, square, cylindrical or other appropriate forms. The material of the droplet removal chamber 4 can be metal, ceramic, plastic or any other waterproof materials. Moreover, the droplet removal chamber 4 also can be made of wood with waterproof coating or similar materials, and a variety of which are well-known to those skilled in the art.

Along the airflow direction, the ROS generator 8 is located in front of the droplet filter 9. Droplets in the airflow are intercepted by the droplet filter 9, which can be an adsorption and/or a scrubber type. The ROS released by ROS generator 8 are actively transferred by the airflow towards the droplet filter 9 for deodorization and disinfection of the contaminated droplets trapped on the droplet filter 9. The aggregated droplets are discharged from the chamber through the water exhaust outlet 7.

FIG. 3 shows the structure of the droplet removal chamber 4 with adsorption droplet filter 9. The adsorption droplet filter 9 is located inside the droplet removal chamber 4. All airflow must pass through the adsorption droplet filter 9 without leakage. The adsorption droplet filter 9 can be metal net, metal frame, metal frame with honeycomb structure, baffle, sponge, foam, porous ceramics, porous activated carbon, fibers and cellulose, which have porous structure and high water adsorption capacity. Droplets from the airflow are adsorbed on the pores of the adsorption materials and aggregate to form large droplets, which are then discharged through the water exhaust outlet 7. The adsorption droplet filter 9 can be cooled down by a cooling system to increase droplet removal efficiency due to condensation.

A valve is installed at the water exhaust outlet 7 for regulating water discharge. The adsorption material of the adsorption droplet filter 9 is impregnated with deodorizing and disinfecting elements in form of powders or granules. After certain period of time, the adsorption droplet filter 9 will be washed for further use or replaced by a clean one.

Figure 4:
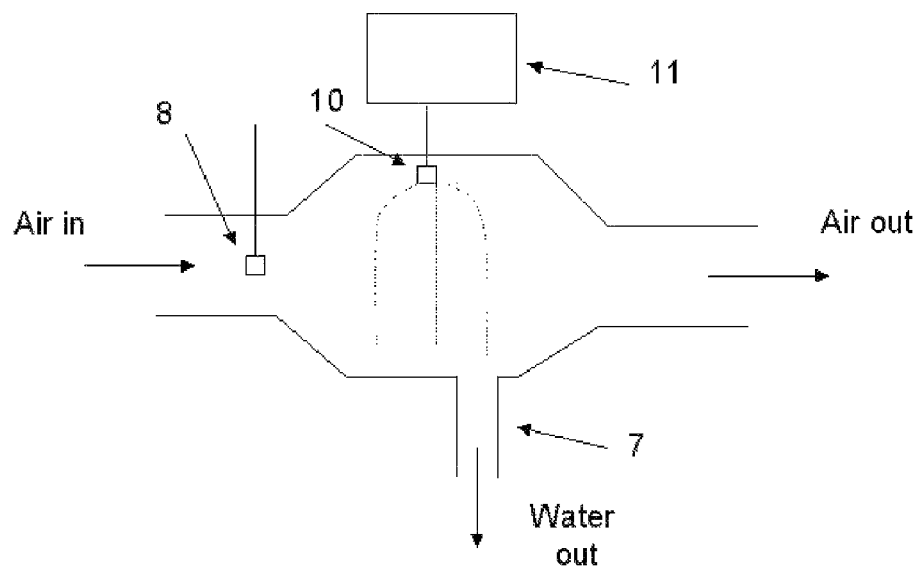
FIG. 4 is a schematic diagram of droplet removal chamber with scrubber according to one embodiment of the present invention.
Figure 5:
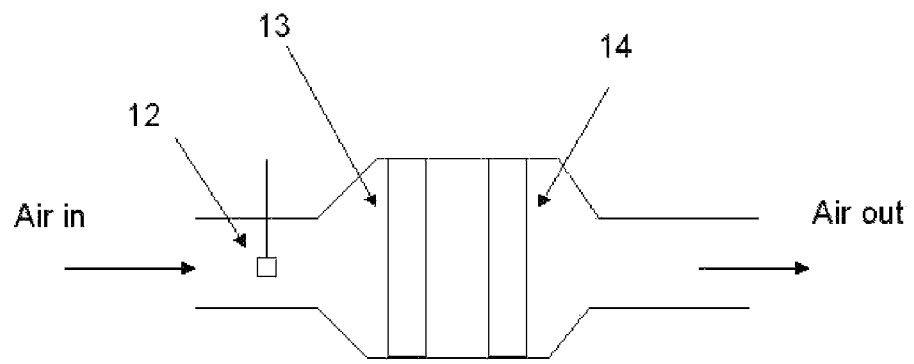
FIG. 5 is a schematic diagram of deodorization and disinfection chamber according to one embodiment of the present invention.

FIG. 4 shows the structure of the droplet removal chamber 4 with a scrubber. A nozzle 10 connected with a water tank 11 is installed in droplet removal chamber 4 to generate a water spray with a size from 10 to 100 micrometer. A valve is installed between the water tank 11 and nozzle 10 for regulating the release of the water spray. When contaminated air passes into the droplet removal chamber 4, the nozzle 10 releases the water spray. Droplets from airflow are intercepted with such water spray to form large droplets, which are too heavy to suspend in air and eventually drop down to the bottom of the droplet removal chamber 4. Then the aggregated droplets are discharged through the water exhaust outlet 7. A valve is installed at the water exhaust outlet 7 for regulating water release. The water in the water tank 11 is mixed with disinfectant and deodorization agents like ozone, chlorine and/or bleaching solution for enhancing disinfection and deodorization capacity. Through the water exhaust outlet 7, the aggregated droplets can be directed to either urinal for cleaning and sterilizing or the water tank 11 for further use.

In another embodiment of the present invention, a plurality of nozzles 10 connected with one or more water tanks are installed in droplet removal chamber 4 to generate a plurality of water sprays each with a size from 10 to 100 micrometer. A valve is installed at the water exhaust outlet 7 for regulating water release.

As droplets are removed in the droplet removal chamber 4, contaminated air is delivered into the deodorization and disinfection chamber 5. As indicated in the FIG. 5, the deodorization and disinfection chamber 5 encloses a ROS generator 12, a dust filter 13 and an adsorbent filter 14. The shape of the deodorization and disinfection chamber 5 can be rectangular, square, cylindrical or other appropriate forms. The material of the deodorization and disinfection chamber 5 can be metal, ceramic, plastic or any other waterproof materials. Moreover, the deodorization and disinfection chamber 5 also can be made of wood with waterproof coating or similar materials, and a variety of which are well-known to those skilled in the art.

Along the airflow direction, the ROS generator 12 is located in front of the dust filter 13 while the adsorbent filter 14 is located behind the dust filter 13. All airflow must pass through the filters without leakage.

The dust filter 13 comprising of fibrous or cellulose materials is used for trapping dust, bacteria and virus. The dust filter 13 can be a HEPA and/or an electrostatic filter.

Figure 6:
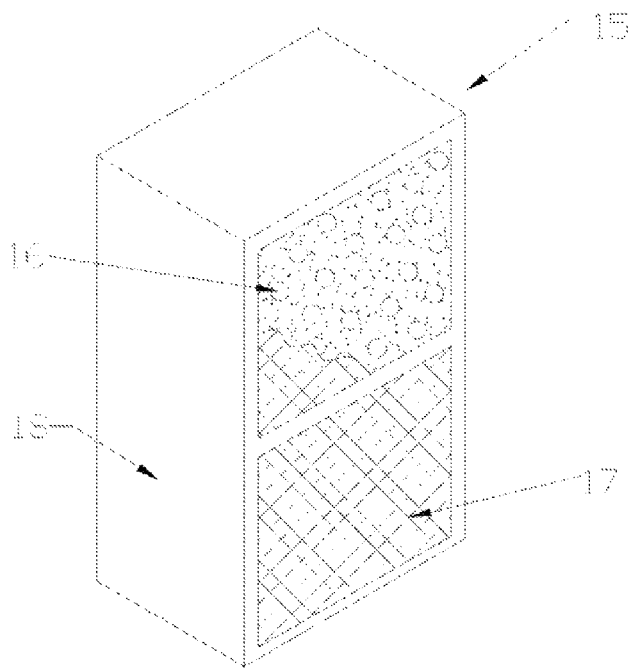
FIG. 6 is a schematic diagram of adsorbent filter according to one embodiment of the present invention.

FIG. 6 shows the structure of the adsorbent filter 14 according to one embodiment of the present invention. The adsorbent filter 14 comprising of porous enclosure 15 and adsorbent materials 16 is used to adsorb gaseous contaminants. The adsorbent materials 16 are impregnated into the porous enclosure 15 which comprises of at least one covering layer 17 and a framework 18. The pore size of covering layer 17 is smaller than the diameter of the adsorbent materials 16 for preventing the loss of adsorbent materials 16, while at the same time it is large enough to allow airflow passing through into the adsorbent filter 14. The materials of the covering layers 17 can be plastic net, metal net, cloth, HEPA and foam. The framework 18 forms the shape of and provides mechanical support to the adsorbent filter 14. The materials of the framework 18 can be metal, paper, wood, plastic or other suitable materials.

The shape of the adsorbent materials 16 can be spherical, cylindrical, rectangular, irregular or in the form of pellet or granule. The size of adsorbent materials 16 is in the range of 1 to 10 mm. The adsorbent materials 16 can be activated carbon, zeolite, metal oxide framework, alumina, silica or in mixture of the aforementioned adsorbent materials. It was known that air contaminants commonly found in toilets are with size between 4 to 20 Angstrom so that the pore size of the adsorbent materials 16 is tuned in the range of 4 to 20 Angstrom for effective adsorption. The property of the adsorbent materials 16 can either be hydrophobic or hydrophilic or in physical mixture of both for efficient adsorption of air contaminants with both types. Transition metals can be incorporated into the porous structure of the adsorbent materials 16 so as to enhance the decomposition rate of air contaminants thanks to their catalytic properties.

The ROS released by ROS generator 12 are actively transferred by the airflow towards the adsorbent filter 14 for decomposition of air contaminants and disinfection. When delivered to the dust filter 13, ROS eradicate bacteria and virus trapped on the dust filter 13 thus avoiding secondary pollution. ROS decompose gaseous contaminants confined within the micro/nanopore of adsorbent materials 16 into non-harmful products like water molecules and carbon dioxide. As the water molecules and carbon dioxide are too small to be retained inside the pores, they are released form the pores and the adsorbent materials 16 are rejuvenated. Hence both dust filter 13 and adsorbent filter 14 are rejuvenated for further adsorption without causing secondary pollution. The ROS generator 12 can be ion generator, charged particle generator, ozone generator, peroxide generator, radical generator such as hydroxyl radical, reactive oxidizing gas generator, electrostatic precipitator. The ROS can be cation, anion, charged particles, ozone, peroxide, radicals such as hydroxyl radical, or any other reactive oxidizing gases. ROS can be generated by electrical method such as electrostatic precipitator and corona discharge, chemical and photolytic method such as UV. Excessive ROS are easily confined and decomposed by the adsorbent filter 14 for avoiding leakage. The choice and amount of ROS are determined by the nature and amount of air contaminants. UV light emitter can be installed in the disinfection chamber 5 for eradication of bacteria and virus and generation of ROS like hydroxyl radical.

The treated air can be either directly discharged through the air outlet 3 or redirected back to the urinal or toilet bowl for further circulation.

The air cleaning apparatus is controlled by an electronic circuit and an infrared sensor. The electronic circuit is to control the air delivery unit 6, ROS generators 8, 12 and valves while the infrared sensor controls the switching system. When there are users, the sensor can sense them and trigger the electronic circuit to switch on the apparatus automatically or vice versa.

Figure 7:
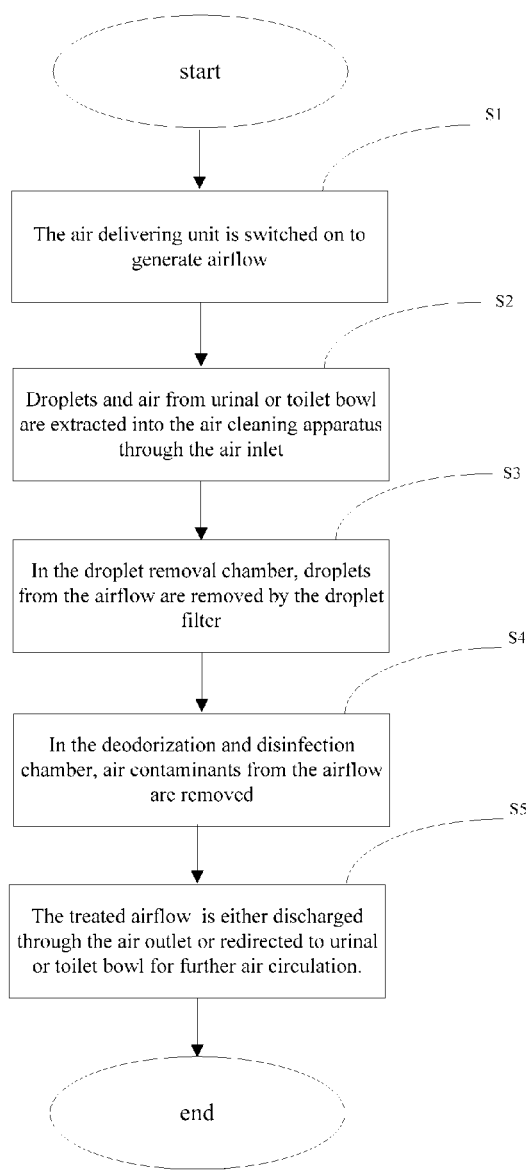
FIG. 7 is an operation flow chart of the air cleaning apparatus according to one embodiment of the present invention.

FIG. 7 is an operation flow chart of the air cleaning apparatus according to one embodiment of the present invention. The method of present invention can be implemented by employing the air cleaning apparatus discussed above, and comprises of following steps.

In step S1, an air delivering unit is switched on to generate airflow. In such airflow, droplets and air carrying odor, bacteria and virus which can transmit disease are contained.

In step S2, droplets and air from urinal or toilet bowl are extracted into the air cleaning apparatus through the air inlet. In one embodiment according to the present invention, the air delivering unit having the capacity in generation of airflow to extract droplets and air into the housing of the air cleaning apparatus through an air inlet is provided, which is located in urinal and toilet bowl. The position, shape and size of air inlet are well designed to achieve sufficient air extraction thus generating negative pressure for trapping contaminated air without spreading.

In step S3, in the droplet removal chamber, droplets from the airflow are removed by the droplet filter. The droplet filter can be constructed according any of the droplet filter discussed above.

In step S4, in the deodorization and disinfection chamber, odor, bacteria and virus from the airflow are removed. In such embodiment, a deodorization and disinfection chamber enclosing a reactive oxidizing species generator, a dust filter and an adsorbent filter, is to remove gaseous contaminants. The dust filter serves to trap dust, airborne bacteria and virus. The adsorbent filter comprises of a porous enclosure and adsorbent materials, which removes gaseous contaminants by confining them into the micro/nanopore of adsorbent materials. The reactive oxidizing species generator releases reactive oxidizing species to eradicate bacteria and virus trapped on the dust filter and decompose odor trapped on the adsorbent filter into non-harmful products thereby preventing secondary pollution.

In the step S5, the treated airflow is either discharged through the air outlet or redirected to urinal or toilet bowl for further air circulation.

In other embodiment of present invention, other air cleaning apparatus discussed above can be used to perform the operation flow chart disclosed in FIG. 7.

By employing the method and an apparatus for deodorizing and disinfecting air according the present invention, odor, bacteria and virus in toilet is removed without causing secondary pollution.

The foregoing description is just the preferred embodiment of the invention. It is not intended to limit the invention. Any modifications, variations, and amelioration without departing from the spirit and scope of the present invention should be included in the scope of the prevent invention.

The invention claimed is:

1. An air cleaning apparatus comprising a housing having one or more air inlets provided for air extraction and an air outlet, wherein the housing encloses a droplet removal chamber for removing droplets from airflow, a deodorization and disinfection chamber for removing air contaminants in the airflow and an air delivery unit for airflow generation, wherein the droplet removal chamber have a water exhaust outlet and encloses a ROS generator and a droplet filter, the deodorization and disinfection chamber encloses an adsorbent filter, a dust filter located in front of the adsorbent filter along the airflow direction, and a ROS generator located in front of the dust filter along the airflow direction, the treated airflow is either discharged or redirected to urinal or toilet bowl for further circulation; ROS released by the ROS generator are actively transferred by the airflow towards the adsorbent filter for decomposition of air contaminants and disinfection, and when delivered to the dust filter, ROS eradicate bacteria and virus trapped on the dust filter thus avoiding secondary pollution, wherein both the dust filter and adsorbent filter are rejuvenated for further adsorption without causing secondary pollution.

2. The air cleaning apparatus according to claim 1, wherein, when such air cleaning apparatus is installed in a toilet, the air inlets are located in urinal or toilet bowl for air extraction.

3. The air cleaning apparatus according to claim 2, wherein, the air contaminants in urinal and toilet bowl are drawn into the air inlets by the airflow.

4. The air cleaning apparatus according to claim 3, wherein, the air contaminants are odor, airborne bacteria and virus released from urine and fecal matter.

5. The air cleaning apparatus according to claim 4, wherein, the contaminants are in the form of droplets and gaseous phase.

6. The air cleaning apparatus according to claim 5, wherein, the size of droplets is from 1 micrometer and 3 millimeter.

7. The air cleaning apparatus according to claim 2, wherein, a negative pressure is generated inside the urinal and toilet bowl by the airflow in order to avoid spreading of air contaminants.

8. The air cleaning apparatus according to claim 1, wherein, the shape of the droplet removal chamber is rectangular, square, or cylindrical and/or the materials of chamber are metal, plastic or ceramic.

9. The air cleaning apparatus according to claim 1, wherein, there are two types of droplet filter used individually or in both.

10. The air cleaning apparatus according to claim 9, wherein, the two types of droplet filter are an adsorption filter and a scrubber.

11. The air cleaning apparatus according to claim 10, wherein, the adsorption droplet filters are metal net, metal frame, metal frame with honeycomb structure, baffle, sponge, foam, porous ceramics, porous activated carbon, fibers and cellulose.

12. The air cleaning apparatus according to claim 10, wherein, the adsorption droplet filter has a porous structure and high water adsorption capacity for trapping droplets in air.

13. The air cleaning apparatus according to claim 12, wherein, the droplets are adsorbed on the pores of the porous structure.

14. The air cleaning apparatus according to claim 13, wherein, a cooling system is provided to increase droplet removal efficiency due to condensation.

15. The air cleaning apparatus according to claim 13, wherein, the droplets aggregate to form large droplets.

16. The air cleaning apparatus according to claim 15, wherein, the large droplets are discharged through the water exhaust outlet.

17. The air cleaning apparatus according to claim 10, wherein, the adsorption filter is made up of adsorption materials which is impregnated with deodorizing and disinfecting elements in form of powders or granules.

18. The air cleaning apparatus according to claim 10, wherein, after certain period of time, the adsorption filter is washed for further use or replaced by a new one.

19. The air cleaning apparatus according to claim 10, wherein, the droplet removal chamber is equipped with at least one nozzle.

20. The air cleaning apparatus according to claim 19, wherein, each of the at least one nozzle is connected with a water tank to generate a water spray with a size from 10 to 100 micrometer.

21. The air cleaning apparatus according to claim 20, wherein, at least one valve is provided to control the release of water spray from the at least one nozzle.

22. The air cleaning apparatus according to claim 20, wherein, the water spray intercepts with droplet contaminants from airflow to form large droplets.

23. The air cleaning apparatus according to claim 20, wherein, the water spray is mixed with disinfectant and/or deodorization agent.

24. The air cleaning apparatus according to claim 23, wherein, the disinfectant and deodorization agent comprises: ozone, chlorine and bleaching solution.

25. The air cleaning apparatus according to claim 22, wherein, the droplets are discharged through the water exhaust duct.

26. The air cleaning apparatus according to claim 25, wherein, the droplets are directed to a urinal or toilet bowl through the water exhaust duct for cleaning and sterilizing or directed to the water tank for further use.

27. The air cleaning apparatus according to claim 1, wherein, the shape of the chamber is rectangular, square, or cylindrical and/or the materials of chamber are metal, plastic or ceramic.

28. The air cleaning apparatus according to claim 1, wherein, the dust filter is for trapping dust, bacteria and virus.

29. The air cleaning apparatus according to claim 28, wherein, the dust filters are HEPA and/or electrostatic filters.

30. The air cleaning apparatus according to claim 1, wherein, the adsorbent filter is for adsorbing gaseous contaminants.

31. The air cleaning apparatus according to claim 30, wherein, the adsorbent filter comprises of a porous enclosure with adsorbent materials impregnated in.

32. The air cleaning apparatus according to claim 31, wherein, the porous enclosure comprises of a framework and at least one covering layer covering the framework.

33. The air cleaning apparatus according to claim 32, wherein, wherein the covering layer has pores to allow airflow passing into the adsorbent filter.

34. The air cleaning apparatus according to claim 32, wherein, the pore size of covering layer is smaller than the diameter of the adsorbent materials for preventing the loss of adsorbent materials.

35. The air cleaning apparatus according to claim 32, wherein, the materials of the covering layers are plastic net, metal net, cloth, HEPA or foam.

36. The air cleaning apparatus according to claim 32, wherein, the framework forms shape and provides mechanical support to the absorbent filter.

37. The air cleaning apparatus according to claim 36, wherein, the materials of framework are metal, paper, wood or plastic.

38. The air cleaning apparatus according to claim 31, wherein, the shapes of the adsorbent materials are spherical, cylindrical, rectangular, irregular or in the form of pellet or granule.

39. The air cleaning apparatus according to claim 38, wherein, the adsorbent materials are activated carbon, zeolite, metal oxide framework, alumina, silica or in mixture of the aforementioned adsorption materials.

40. The air cleaning apparatus according to claim 39, wherein, the size of adsorbent materials is in the range of 1 to 10 mm.

41. The air cleaning apparatus according to claim 39, wherein, the adsorbent materials has a micro/nanopore in the range of 4 to 20 Angstrom.

42. The air cleaning apparatus according to claim 39, wherein, the adsorbent materials are hydrophobic, hydrophilic or in a mixture of both.

43. The air cleaning apparatus according to claim 39, wherein, transition metals are incorporated into the porous structure of the adsorbent materials.

44. The air cleaning apparatus according to claim 1, wherein a UV light emitter is installed in the deodorization and disinfection chamber for eradication of bacteria and virus by UV light and generation of ROS.

45. The air cleaning apparatus according to claim 1, wherein, the ROS are cation, anion, charged particles, ozone, peroxide, radicals or reactive oxidizing gases.

46. The air cleaning apparatus according to claim 45, wherein, the ROS generator includes any one of the listed generators: ion generator, charged particle generator, ozone generator, peroxide generator, radical generator, reactive oxidizing gas generator and electrostatic precipitator.

47. The air cleaning apparatus according to claim 45, wherein, the ROS can be generated by electrical, chemical or photolytic method.

48. The air cleaning apparatus according to claim 45, wherein, the choice and amount of ROS are determined by the nature and amount of air contaminants.

49. The air cleaning apparatus according to claim 48, wherein, the ROS decompose the air contaminants confined in the micro/nanopores of the adsorbent materials into non-harmful products.

50. The air cleaning apparatus according to claim 49, wherein, the micro/nanopores of the adsorbent materials are rejuvenated by the ROS for further adsorption.

51. The air cleaning apparatus according to claim 45, wherein, the adsorbent materials confine and decompose excessive ROS for avoiding leakage.

52. The air cleaning apparatus according to claim 1, wherein, the air cleaning apparatus is controlled by an electronic circuit and an infrared sensor.

53. The air cleaning apparatus according to claim 52, wherein, the electronic circuit controls the air delivery unit, ROS generator and valves.

54. The air cleaning apparatus according to claim 52, wherein, the infrared sensor controls the switching of the air cleaning apparatus depending on whether there is a user.

55. A method for disinfecting and deodorizing a toilet system by employing an air cleaning apparatus comprising a housing having one or more air inlets provided for air extraction and an air outlet, wherein the housing encloses a droplet removal chamber for removing droplets from airflow, a deodorization and disinfection chamber for removing air contaminants in the airflow and an air delivery unit for airflow generation, wherein the droplet removal chamber have a water exhaust outlet and encloses a ROS generator and a droplet filter, the deodorization and disinfection chamber encloses an adsorbent filter, a dust filter located in front of the adsorbent filter along the airflow direction, and a ROS generator located in front of the dust filter along the airflow direction, the treated airflow is either discharged or redirected to urinal or toilet bowl for further circulation; ROS released by the ROS generator are actively transferred by the airflow towards the adsorbent filter for decomposition of air contaminants and disinfection, and when delivered to the dust filter, ROS eradicate bacteria and virus trapped on the dust filter thus avoiding secondary pollution, wherein both the dust filter and adsorbent filter are rejuvenated for further adsorption without causing secondary pollution;

said method comprising the steps:
a) The air delivering unit is switched on to generate airflow;
b) Droplets and air from urinal or toilet bowl are extracted into the air cleaning apparatus through the air inlet;
c) In the droplet removal chamber, droplets from the airflow are removed by the droplet filter;
d) In the deodorization and disinfection chamber, air contaminants from the airflow are removed;
e) The treated airflow is either discharged through the air outlet or redirected to urinal or toilet bowl for further circulation.

* * * * *

UNITED STATES PATENT AND TRADEMARK OFFICE
CERTIFICATE OF CORRECTION

PATENT NO.        : 8,709,137 B2
APPLICATION NO.   : 13/395447
DATED             : April 29, 2014
INVENTOR(S)       : Chi Keung Rudy Chan et al.

Page 1 of 1

It is certified that error appears in the above-identified patent and that said Letters Patent is hereby corrected as shown below:

On the title page item (73) should read:
Assignee: RHT LIMITED, Fo Tan, N.T, Hong Kong (CN)

Signed and Sealed this
Eleventh Day of August, 2015

Michelle K. Lee
*Director of the United States Patent and Trademark Office*